United States Patent [19]

O'Neil

[11] Patent Number: 4,620,544
[45] Date of Patent: Nov. 4, 1986

[54] VACUUM EXTRACTOR

[75] Inventor: Alexander G. B. O'Neil, 102 Lawler Street, Subiaco 6008, Perth, Western Auxtralia, Australia

[73] Assignees: Alexander G. O'Neil; Christine O'Neil, both of Perth, Australia

[21] Appl. No.: 761,678

[22] PCT Filed: May 28, 1981

[86] PCT No.: PCT/GB81/00094
§ 371 Date: Jan. 25, 1982
§ 102(e) Date: Jan. 25, 1982

[87] PCT Pub. No.: WO81/03420
PCT Pub. Date: Dec. 10, 1981

Related U.S. Application Data

[63] Continuation of Ser. No. 645,097, Aug. 22, 1984, abandoned, which is a continuation of Ser. No. 355,551, Jan. 25, 1982, abandoned.

[30] Foreign Application Priority Data

May 29, 1980 [GB] United Kingdom ............... 8017621

[51] Int. Cl.⁴ .......................................... A61B 17/42
[52] U.S. Cl. .................................. 128/352; 128/361
[58] Field of Search ............... 128/361, 352, 323, 324, 128/303 R; 604/73–75, 313–316; 114/253; 294/64 R

[56] References Cited

U.S. PATENT DOCUMENTS

| 13,453 | 8/1855 | Buffum | 128/352 |
|---|---|---|---|
| 2,227,673 | 1/1941 | Price | 128/352 |
| 2,702,038 | 2/1955 | Uddenberg | 128/361 |
| 2,871,054 | 1/1959 | Zinke | 294/64 R |
| 4,166,648 | 9/1979 | Creskoff | 294/64.1 |
| 4,512,347 | 4/1985 | Uddenberg | 128/352 |

FOREIGN PATENT DOCUMENTS 118578 11/1959 U.S.S.R. ........................... 128/361

OTHER PUBLICATIONS

J. Lovset, "Vaginal Operative Delivery" (Scandanavian University Books, 1968).

Primary Examiner—C. Fred Rosenbaum
Assistant Examiner—Gene B. Kartchner
Attorney, Agent, or Firm—Mason, Fenwick & Lawrence

[57] ABSTRACT

A vacuum extractor for use in childbirth has an evacuable suction cup for engaging the child's scalp, the cup being connected to a source of a pulling force in a manner which ensures that the line of the force passes substantially through the center of the cup's lip, thereby minimizing the production of tilting moments on the cup on application of an oblique pulling force.

5 Claims, 4 Drawing Figures

VACUUM EXTRACTOR

This application is a continuation of application Ser. No. 645,097, filed Aug. 22, 1984, now abandoned, which is a continuation of application Ser. No. 355,551, filed Jan. 25, 1982, now abandoned.

This invention relates to a vacuum extractor.

The vacuum extractor has been well accepted as having a useful place in modern obstetrics since Malström's cup was introduced in 1954. John Yonge (1706) had first tried to use a suction device but his instrument met with very little success. The vacuum found a place in clinical practice again in 1947 with Couzigous' ventouse eutocique in France, and Koller's instrument in Norway in 1950.

Since then the instrument has been improved by a number of workers. Lovset in 1965 suggested modifying the vacuum, by making one side of the vacuum cup thinner, moving the suction connection from the centre to the edge of the cup, and applying traction to the cup from four equally-spaced points at the peripheries of the cup. These points were attached to two loops of cord, each of which had its own block attached. The two blocks were then joined by a further loop which had a further block attached to it. However this arrangement was not considered practical, and did not gain wide acceptance.

In 1969, Bird suggested applying traction to the cup by a chain llinked to a small, centrally situated half ring. The peripherally placed vacuum suction tubing was connected to his cup in a similar manner to Lovset's cup.

In modern obstetrics the vacuum cups designed by Bird and Malstrom have gained wide acceptance. Both of these cups have the intrinsic disadvantage of producing a rotational force, causing one edge of the cup to lift while the other remains the fulcrum. The problem is illustrated in FIG. 1 of the accompanying drawings in which:

F=Traction required to break the vacuum.
A=Effective lifting force on fetal head.
B=Sliding force.
C=Rotational force acting on point E.
P=Vacuum pressure attaching vacuum to fetal head.

By vector analysis the force required to break the vacuum can be calculated using the formula:

$$F = [(\pi R^3 P)/(X \sin \phi + R \cos \phi)]$$

The force (A) which effectively lifts the baby can be calculated using the formula:

$$A = F \cos \phi$$

This has to be computed for angles from 0° to 45° from the perpendicular. With a 5 cm Bird cup, the effective traction on the baby is approximately 50% when the direction of pull is 45° from the perpendicular axis.

Most clinicians are aware of the problem and so attempt to pull at 90° to the surface of the cup. As this is not always possible, the experienced clinician is able to apply force at the margin of the cup.

These rotational forces introduce unnecessary tissue trauma and decrease the effective lifting force of the vacuum cup.

According to the present invention there is provided a vacuum extractor having a cup shaped member for forming an air-tight seal around its lip in use and having means through which its interior can be evacuated in use, elongate connection means for transferring an applied force to the cup-shaped member, and adaptor means through which the connection means is attached to the cup-shaped member, the adaptor means being adapted and arranged so that the line of a force exerted on the cup through the connection means passes through or adjacent the centre of a closed figure defined by the lip of the cup-shaped member over a range of angles between the line of force and a line normal to the plane of the closed figure.

The adaptor means may be attached to the connection means through a ring or hook for attachment of a chain, cord, string, plastics extrusion or the like. The ring or hook may be slidable on an arcuate rod, the centre of the rod's arc being at or adjacent the centre of the closed figure defined by the lip of the cup-shaped member. The rod itself may be rotatable on the cup-shaped member so that the rod describes part of the surface of an imaginary sphere centred at or adjacent the centre of the closed figure. The rod may extend rigidly from a ring or plate freely rotatable on the base of the cup-shaped member.

Alternatively the adaptor means can be provided by a cord, string or other elongate flexible member extending from the cup-shaped member at its opposed sides. Again, the connection means is attached to the adaptor means so as to be movable along it.

The adaptor means may comprise a second elongate flexible member secured at each end of the cup-shaped member at diametrically opposed locations intermediate the locations at which the first flexible member is secured, and the first and second flexible members are interconnected by a sliding connector to which the connection means is attached.

The cup-shaped member may be of rubber, plastics, metal or other suitable material. The adaptor means is preferably in such a form that forces can be applied at angles between 0° and 30° in any direction to the line normal to the plane of the closed figure defined by the lip of the cup-shaped member, although greater or lesser ranges can be provided if required, for example by increasing or decreasing the radius of the sphere on whose surface the attachment between the connection means and the adaptor means may lie.

Embodiments of the invention will now be described by way of example with reference to the accompanying drawings, in which.

Figure 1:
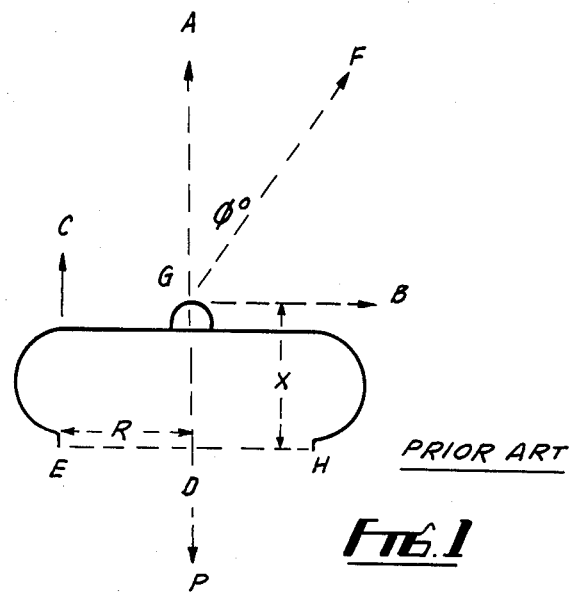
FIG. 1 is a schematic side view of a prior art vacuum extractor showing the origin of tilting forces on the cup when an angled pull is applied.
Figure 2:
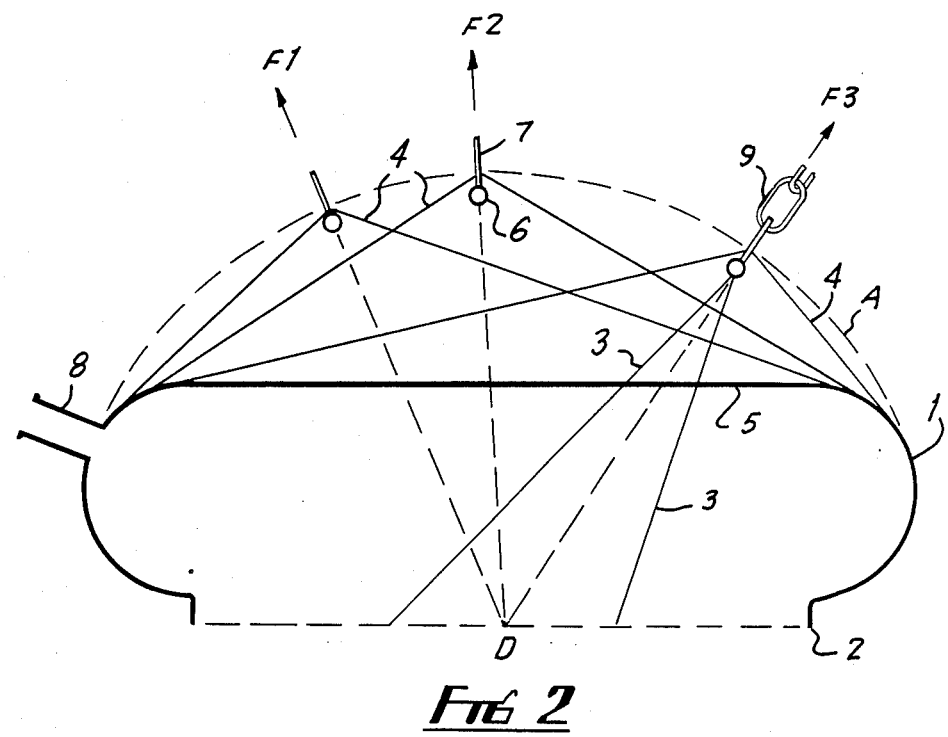
FIG. 2 is a schematic diagram of an extractor of this invention.

Referring to FIG. 2, the extractor of this embodiment of the invention has a rubber cup-shaped member 1 having a round annular lip 2. Securely attached to the side faces of the cup 1 are a pair of cords 3 and 4 disposed so as to extend across the base 5 of the cup 1 at right-angles to one another. First and second metal rings 6 and 7 encircle the cords 3 and 4 respectively, and also pass through one another, and a length of chain 9 is attached at one end to the ring 7, its other end being free.

The first cord 3 is 4 mm shorter than the second cord 4; the first ring 6 is of 3 mm diameter while the second ring is of 6 mm diameter.

A tube 8 leads through the side wall of the cup-shaped member 1 and provides a connection for a vacuum pump (not shown).

In use, the cup 1 is held with its annular lip 2 on the surface of a baby's head prior to delivery, with the lip 2 forming an air-tight seal against the head. The tube 8 has already been connected to a vacuum pump, and this is now switched on, evacuating the interior of the member 1 to seat it firmly on the baby's head. The obstetrician grips the free end of the chain 9 and pulls it, applying traction to the ring 7 in a direction F1, F2 or F3. The rings 6 and 7 slide along their respective cords 3 and 4 under the effect of the traction in each case to the positions shown in FIG. 2 so that the line of applied force F1, F2, F3 passes through a point D lying at the centre of the circle defined by the lip 2. In this way traction is applied to the baby's head through the cup 1 without causing rotational forces on the cup 1, even though the line of applied force is not at right-angles to the base of the cup. The interaction of the cords 3 and 4 ensures that the rings 6 and 7 are constrained to move on the surface of an imaginary sphere centred on the point D, as shown by the dotted line A.

Figure 3:
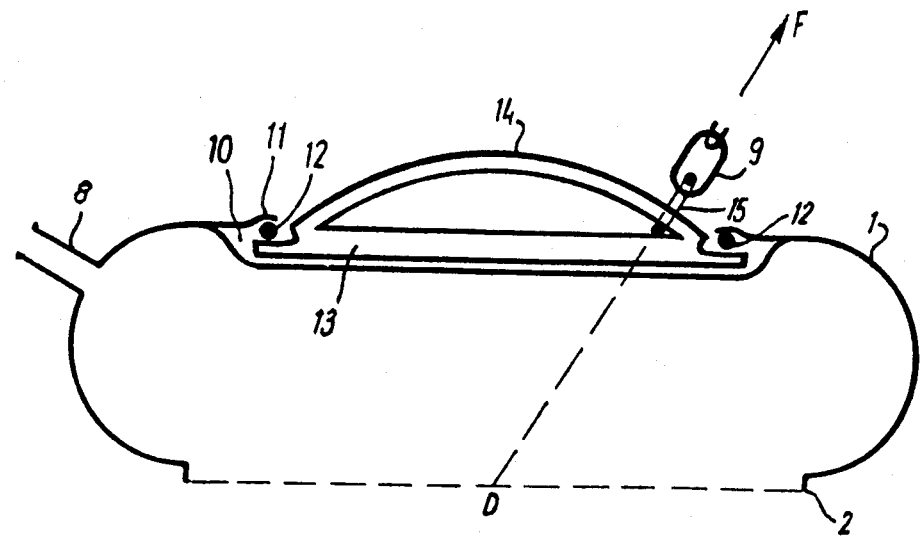
FIG. 3 is a side sectional view of another extractor of the invention.

Referring now to FIG. 3, the cup 1 is of stainless steel and its side wall is generally of the same shape as that in FIG. 2. However, its base is recessed at 10, with a peripheral inwardly facing flange 11 around it. An annular bearing 12 is located in the recess 10 below the flange 11 by which it is held in place, and a circular metal plate 13 has its periphery in engagement with the bearing 12 so as to be rotatable within the recess 10.

The plate 13 has a diametrically-directed arcuate rod 14 formed integrally with it, the centre of the rod's arc being at point D, the centre of the circle defined by the annular lip 2 of the cup 1. A ring 15 is loosely held on the rod 14 and is slidable along it, and a metal chain 9 is attached to the ring 15 for applying traction.

The extractor of FIG. 3 is used in similar fashion to that of FIG. 2. The tube 8 is connected through a rubber hose to an air pump and the cup 1 is placed on the head of a baby to be delivered, so as to form an air-tight seal around its lip 2. Suction is applied from the pump to reduce the pressure of air within the cup 1, and traction is applied by the obstetrician pulling on the free end of the chain 9 in a direction F. Under the effect of this force F the ring 15 slides along the rod 14, and the plate 13 rotates on its bearing 12, until the line of the force F passes through the point D. In this position equilibrium is achieved, and if the angle of the line of force F is changed, by the obstetrician altering the position of the free end of the chain 9, the ring 15 slides on the rod 14 and the plate 13 rotates until equilibrium is re-established by the new line of force passing through the point D. The arrangement is therefore self-aligning.

By providing an arrangement which ensures that the line of applied force F always passes through the centre D of the closed figure defined by the lip 2 of the cup-shaped member 1, rotational forces about an axis in the plane of the closed figure are minimised or eliminated, and the tendency for the cup 1 to tilt and break the air-tight seal with the baby's head is correspondingly reduced. The ease and success of traction during delivery is thus greatly enhanced, so the extractors of this invention as shown in FIGS. 2 and 3 provide a valuable tool for the obstetrician. Further, this result has been achieved in a simple and inexpensive apparatus which can be made either disposable or re-usable depending on the materials of manufacture selected.

Using such vacuum apparatus of the invention the effective lifting force resulting from the vacuum within the cup 1 is maintained at all angles of the line of force F; the applied force required to break the seal between the lip 2 and the baby's head increases with the angle of the line of force F from a line normal to the baby's head, or vacuum surface.

Figure 4:
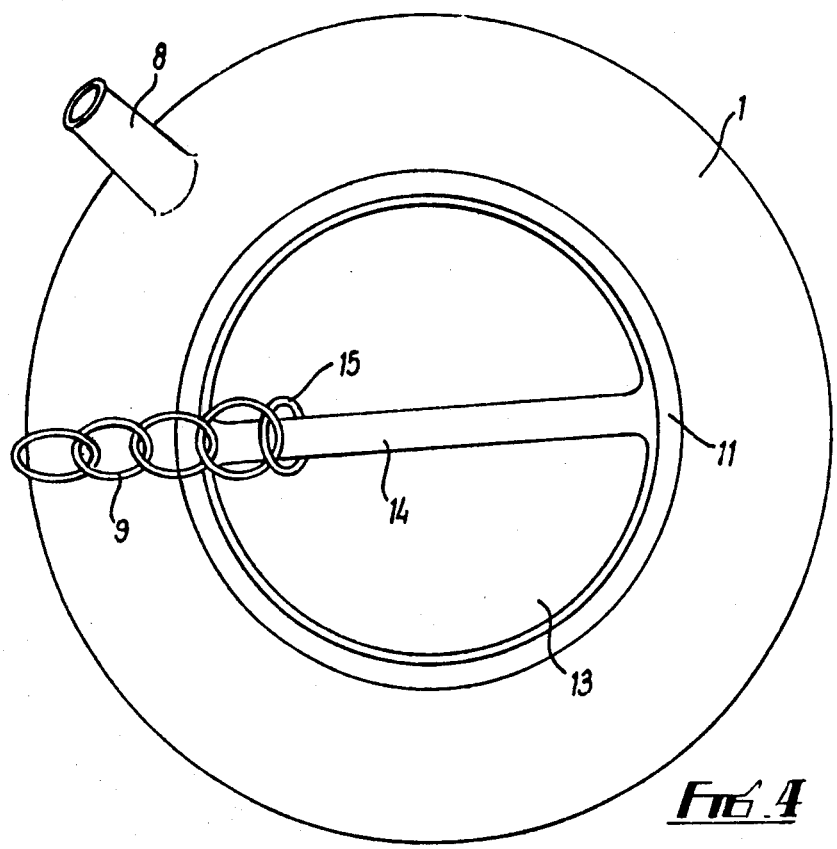

FIG. 4 is a plan view of the extractor of FIG. 3.

Modifications and improvements may be made without departing from the scope of the invention.

I claim:

1. A vacuum extractor for use in childbirth, comprising:

a cup-shaped member having a lip, said cup-shaped member when in use forming an air-tight seal around said lip on the scalp of the child;

means disposed in said cup-shaped member through which its interior can be evacuated when in use;

adaptor means comprising an arcuate rod having first and second ends;

means for rotatably attaching said first and second ends of said arcuate rod to said cup-shaped member at diametrically opposed locations, whereby said arcuate rod describes a part-spherical locus, said rod extending rigidly from said attaching means; and connection means for transferring an applied force to said cup-shaped member, said connection means being freely movable on said arcuate rod, whereby the line of force exerted on said cup-shaped member through said connection means passes through or adjacent to the center of a closed figure defined by said lip of said cup-shaped member over a range of angles between the line of force and a line normal to a plane containing the closed figure.

2. A vacuum extractor according to claim 1, wherein said attaching means comprises a plate which is freely rotatable on said cup-shaped member.

3. A vacuum extractor according to claim 1, wherein said attaching means comprises a ring which is freely rotatable on said cup-shaped member.

4. The vacuum extractor of claim 1, wherein said connection means comprises a flexible cord-like member.

5. The vacuum extractor of claim 1, wherein the range of angles between the line of force and the line normal to the plane containing the closed figure is from approximately 0° to approximately 30°.

* * * * *